US006060600A

United States Patent [19]
Chruscial et al.

[11] Patent Number: 6,060,600
[45] Date of Patent: May 9, 2000

[54] SUBSTITUTED TETRONIC ACIDS USEFUL FOR TREATING HIV AND OTHER RETROVIRUSES

[75] Inventors: Robert A. Chruscial, Portage; Linda L. Maggiora; Suvit Thaisrivongs, both of Kalamazoo; James M. Tustin, Richland; Clark W. Smith, Kalamazoo, all of Mich.; Ruben A. Tommasi, Whitehouse Station, N.J.; Paul A. Aristoff, Kalamazoo, Mich.; Harvey I. Skulnick, Kalamazoo, Mich.; W. Jeffrey Howe, Kalamazoo, Mich.

[73] Assignee: Pharmacia & Upjohn Company, Kalamazoo, Mich.

[21] Appl. No.: 08/913,463

[22] PCT Filed: Mar. 7, 1996

[86] PCT No.: PCT/US96/02680

§ 371 Date: Sep. 17, 1997

§ 102(e) Date: Sep. 17, 1997

[87] PCT Pub. No.: WO96/29333

PCT Pub. Date: Sep. 26, 1996

Related U.S. Application Data

[63] Continuation of application No. 08/407,322, Mar. 20, 1995, abandoned.

[51] Int. Cl.$^7$ .................. C07D 491/107; C07D 491/02; C07D 307/00
[52] U.S. Cl. ............................ 546/16; 544/238; 549/331; 549/477; 514/278
[58] Field of Search ............................................. 546/16

[56] References Cited

FOREIGN PATENT DOCUMENTS

| | | |
|---|---|---|
| 0202589 A2 | 11/1986 | European Pat. Off. . |
| 0259707 A2 | 3/1988 | European Pat. Off. . |
| 0365329 A2 | 4/1990 | European Pat. Off. . |
| 0480624 A1 | 4/1992 | European Pat. Off. . |
| 0534907 A1 | 3/1993 | European Pat. Off. . |
| 05043568 | 2/1993 | Japan . |
| WO93/04055 | 3/1993 | WIPO . |
| WO94/11361 | 5/1994 | WIPO ......................... C07D 309/38 |
| WO94/18188 | 8/1994 | WIPO ......................... C07D 311/46 |
| WO95/07901 | 3/1995 | WIPO . |

OTHER PUBLICATIONS

Rehse, K., et al., "Anticoagulant Activity of 3,5–Disubstituted Tetronic Acids," *Arch. Pharm.* (Weinheim) vol. 311, pp. 986–992 (1978).
Rehse, K., and Wagenknecht, J., "Mass Spectrometric Investigation of Anticoagulant 3–(1–Arylpropyl)–tetronic Acids," *Arch. Pharm.* (Weinheim), vol. 312, pp. 164–168 (1979).
Rehse, K., et al., "Protein Binding of Drugs Determined by Continuous Ultrafiltration, III: Protein Binding of Anticoagulant Tetronic Acids," *Arch. Pharm.* (Weinheim) vol. 315, pp. 052–056 (1982).
*J. Synthetic Org. Chem.* Japan, vol. 44, No. 2, pp. 127–(1986).

Vekemans, J., "An Efficient Synthesis of (S)–5–Hydroxymethyl–2(5H)–Furanone" *Tetrahedron Letters*, vol. 28, No. 20, pp. 2299–2300 (1987).
*J. Org. Chem.*, vol. 46, pp. 2299–(1981).
Kokai Number Hei–4–211676, Abstract, published Aug. 3, 1992; Yoji, Shirokura.
Roggo, B. E., et al., "3–Alkanoyl–5–Hydroxymethyl Tetronic Acid Homologues and Resistomycin: New Inhibitors of HIV–1 Protease, I. Fermentation, Isolation and Biological Activity" *J. of Antibiotics*, vol. 47, No. 2, pp. 136–142 (Feb. 1994).
Roggo, B. E., et al., "3–Alkanoyl–5–Hydroxymethyl Tetronic Acid Homologues and Resistomycin: New Inhibitors of HIV–1 Protesase, II. Structure Determination" *J. of Antibiotics*, vol. 47, No. 2, pp. 143–147 (Feb. 1994).
Lang, Marc and Roesel, Johannes, "HIV–1 Protease Inhibitors: Development, Status and Potential Role in the Treatment of AIDS," *Archives of Pharmacy*, vol. 326, pp. 921–924 (1993).
Chemical Abstracts, vol. 98: 119144p, p. 20 (1983).
Chemical Abstracts, vol. 90: 185907a, p. 575 (1979).
Chemical Abstracts, vol. 90: 114925u, p. 28 (1979).
Chemical Abstracts, vol. 55, col. 16687, paragraph f.
Fell, S.C.M. et al. "Synthesis of 4–Substituted Tetronic Acids: Multicolanic Acid." *J. Chem. Soc., Chem. Commun.*, vol. 2, pp. 81–82 (1979).
Chemical Abstracts, vol. 34, Alicyclic Compounds (1963), Col. 2378, paragraph f.
Chemical Abstracts, vol. 118: 45729r, p. 457 (1993).
Sibi M.P. et al., "A Convenient Synthesis of 3–alkyltetronic acids from 3–acyletronic acids." *Synthetic Communications*, vol. 22, No. 6, pp. 809–816 (1992).
Arai K., et al. "Metabolites of *Penicillium italicum* Wehmer: Isolation and Structures of New Metabolites Including Naturally Occurring 4–ylidene–acyltetronic Acids, Italicinic Acid and Italicic Acid." *Chem Pharm. Bull.*, vol. 37, No. 12, pp. 3229–3235 (1989).
Wakabayashi, S., "Synthesis of Optically Active Litsenolide C." *The Chemical Society of Japan. Chemistry Letters* (5) pp. 875–878 (1987).
Buck, J. "Directed Metallations of 4–Ethylidenetetronic Acid O–Methyl Ether and its Derivatives as a Synthetic Entry to Natural 4–Oxyfuran–2–ones." *J. Chem. Soc. Perkin Trans* 1, vol. 11, pp. 2399–2405 (1985).
Vanwagenen, B.S. "Native American Food and Medicinal Plants." *Tetrahedron*, vol. 42, No. 4, pp. 1117–22.
Chemical Abstracts, vol. 97: 109463g (1982).
Anderson J.R., "Metabolites of Higher Fungi . . . " *J. Chem. Soc., Perkin Trans.* 1, vol. 1, pp. 215–221.
Chemical Abstracts, vol. 87: 184299e (1977).
Damon, R.E., et al., "A general synthesis of 2–alkyletronic acids" *Tetrahedron Letters*, vol. 32, pp. 2749–2752.

(List continued on next page.)

*Primary Examiner*—Alan L. Rotman
*Attorney, Agent, or Firm*—Thomas A. Wootton

[57] ABSTRACT

This application discloses novel tetronic acids for the treatment of AIDS and other diseases caused by retroviruses.

7 Claims, No Drawings

OTHER PUBLICATIONS

Gudgeon, J.A., et al, "The Structures and Biosynthesis of Multicolanic, Multicolic and Multicolosic Acis, Novel Tetronic Acid Metabolites of Penicillium Multicolor." *Bioorganic Chemistry*, vol. 8, pp. 311–322 (1979).

Gudgeon, J.A., et al, "Use of singly and doubly labeled carbon–13–acetate in the elucidation of the structures and biosynthesis of multicolic and multicolosic acids, new tetronic acids from Penicillium multicolor." *J. Chem. Soc., Chem. Commun.*, vol. 16, pp. 636–8 (1974).

Sudo, R, et al, "Synthesis of Carolic Acid," *J. Org. Chem.*, vol. 32, No. 6, pp. 1844–6. CA67(5):21426s.

Chemical Abstracts, vol. 63, col. 13064, paragraph "a," (1965).-

SUBSTITUTED TETRONIC ACIDS USEFUL FOR TREATING HIV AND OTHER RETROVIRUSES

This application is the continuation (national phase) of International Application No. PCT/US96/02680, International Filing Date Mar. 7, 1996 which was a continuation patent application of U.S. patent application Ser. No. 08/407,322, filed Mar. 20, 1995, abandoned.

BACKGROUND OF THE INVENTION

1. Field of the Invention

This invention comprises novel substituted tetronic acid type compounds, 2,4-(3H,5H)-furandiones, that are useful for the inhibition of the HIV protease enzyme. The compounds may be useful for the treatment of a person with AIDS or AIDS related diseases. The compounds may be used in the attempt to retard the further replication of any retrovirus containing the aspartyl protease enzyme.

2. Information Disclosure

PCT/US94/09533, filed Sep. 7, 1994.

WO 93/04055, published Mar. 4, 1993, inventor Dolak, Lester, et al. A tetronic acid useful for the inhibition of HIV-protease.

EP 0,259,707-A2 published Mar. 16, 1988, assigned to Takeda Chemical; Terao, Shinji et al., Hydroxybutenolide Derivatives useful for scavenging active oxygen species.

JP 05043568-A (90JP-202268) published Feb. 23, 1993, assigned to Takeda Chemical, disclosing tetronic acids used to treat inflammatory diseases.

Rehse, K., et al., "Anticoagulant Activity of 3,5-Disubstituted Tetronic Acids," *Arch. Pharm.* (Weinheim) Vol. 311, pp. 986–992 (1978).

Rehse, K., and Wagenknecht, J., "Mass Spectrometric Investigation of Anticoagulant 3-(1-Arylpropyl)-tetronic Acids," *Arch. Pharm.* (Weinheim), Vol. 312, pp. 164–168 (1979).

Rehse, K., et al., "Protein Binding of Drugs Determined by Continuous Ultrafiltration, III: Protein Binding of Anticoagulant Tetronic Acids," *Arch. Pharm.* (Weinheim) Vol. 315, pp. 052–056 (1982).

EP 0,534,907-A1, (92JP-276543) published Mar. 31, 1993, assigned to Nippon Zoki Pharmaceutical disclosing 2-(5H)-furanones to treat auto-immune diseases.

*J. Synthetic Org. Chem.* Japan, Vol. 44, No. 2, pp. 127– (1986).

Vekemans, J., "An Efficient Synthesis of (S)-5-Hydroxymethyl-2(5H)-Furanone" *Tetrahedron Letters*, Vol. 28, No. 20, pp. 2299–2300 (1987).

*J. Org. Chem.*, Vol. 46, pp. 2299– (1981).

Kokai Number Hei-4-211676, published Aug. 3, 1992; Yoji, Shirokura. A tetronic acid useful as a vasodilator.

Roggo, B. E., et al., "3-Alkanoyl-5-Hydroxymethyl Tetronic Acid Homologues and Resistomycin: New Inhibitors of HIV-1 Protease, I. Fermentation, Isolation and Biological Activity" *J. of Antibiotics*, Vol. 47, No. 2, pp. 136–142 (Feb. 1994).

Roggo, B. E., et al., "3-Alkanoyl-5-Hydroxymethyl Tetronic Acid Homologues and Resistomycin: New Inhibitors of HIV-1 Protease, II. Structure Determination" *J. of Antibiotics*, Vol. 47, No. 2, pp. 143–147 (February 1994).

Lang, Marc and Roesel, Johannes, "HIV-1 Protease Inhibitors: Development, Status and Potential Role in the Treatment of AIDS," *Archives of Pharmacy*, Vol. 326, pp. 921–924 (1993). Undisclosed tetronic acid-type compounds thought to be possible HIV-1 protease inhibitor.

Chemical Abstracts, Vol. 98: 119144p (1983) page 20, anticoagulant activity of 3-arylalkyl-5-phenyl tetronic acids. 10 tetronic acid derivatives. Registry number of one compound is 80936-00-1, CA index name, 2(5H)-Furanone, 3-(1-(4-chlorophenyl)ethyl)-4-hydroxy-5-methyl-(9CI).

Chemical Abstracts, Vol. 90: 185907a (1979) page 575, Mass spectrometric investigation of anticoagulant 3-(1-arylpropyl) tetronic acids. Tetronic acid derivatives. Registry number of one compound, 69354-72-9, CA index name, 2(5H)-Furanone, 4-hydroxy-5-methyl-3-(1-phenylpropyl)-(9CI).

Chemical Abstracts, Vol. 90: 114925u (1979) page 28, Anticoagulant activity of 3-5-disubstituted tetronic acids. Tetronic acid derivatives. Registry number of one compound, 69354-71-8, CA index name, 2(5H)-Furanone, 3-(1-(4-chlorophenyl)propyl)-4-hydroxy-5-methyl-(9CI).

Chemical Abstracts, Vol. 55, Column 16687, paragraph f, disclosure of 3-(1-aminoethyl)-5-methyltetronic acid. Registry number 89910-36-1. CA index name, valeric acid, 2-(1-aminoethyl)-4-hydroxy-3-oxo, .gamma.-lactone (6CI, 7CI).

Fell, S. C. M. et al. "Synthesis of 4-Substituted Tetronic Acids: Multicolanic Acid." *J. Chem. Soc., Chem. Commun.*, Vol. 2, pp. 81–2 (1979).

Chemical Abstracts, Vol. 34, Alicyclic Compounds (1963), Column 2378, paragraph f, disclosure of ethyl and methyl benzyltetronic acid. Registry number 91910-33-7. CA index name, valeric acid, 2 ethyl-4-hydroxy-3-oxo-5-phenyl, .gamma.-lactone (7CI).

Chemical Abstracts, Vol. 118: 45729r (1993) page 457, vasodilators containing terpenes, Registry number 145298-30-2, -29-9, -28-8, -27-7 CA index names, 2(5H)-Furanone, 3-(3,7-dimethyl-2,6octadienyl)-4-hydroxy-5-(3-methyl-2-butenyl)-(9CI); 2(5H)-Furanone, 3-(3,7-dimethyl-2, 6octadienyl)-4-methoxy-5-(3-methyl-2-butenyl)-(9CI); 1,3-Pentanedione, 1-(4-(3,7-dimethyl-2,6-octadienyl)-2,5-dihydro-3-methoxy-2-(3-methyl-2-butenyl)-5-oxo-2-furanyl)-4-methyl-2-(3-methyl-2-butenyl)-(9CI); 1,3-Pentanedione, 1-(4-(3,7-dimethyl-2,6-octadienyl)-2,5-dihydro-3-hydroxy-2-(3-methyl-2-butenyl)-5-oxo-2-furanyl)-4-methyl-2-(3-methyl-2-butenyl)-(9CI).

Sibi, M. P. et al., "A Convenient Synthesis of 3-alkyltetronic acids from 3-acyltetronic acids." *Synthetic Communications*, Vol. 22, No. 6, pp. 809–816 (1992). Reductive deoxygenation of 3-acyltetronic acids provides 3-alkyltetronic acids in high yields. CA index names, 2(5H)-Furanone, 4-hydroxy-5-methyl-3-(2-methylpropyl)-, (S)-(9CI); 2(5H)-Furanone, 3-butyl-4-hydroxy-5-methyl, (S)-(9CI); 2(5H)-Furanone, 4-hydroxy-5-methyl-3-propyl-, (S)-(9CI); 2(5H)-Furanone, 3-ethyl-4-hydroxy-5-methyl, (S)-(9CI).

Arai, K., et al. "Metabolites of *Penicillium italicum* Wehmer: Isolation and Structures of New Metabolites Including Naturally Occurring 4-ylidene-acyltetronic Acids, Italicinic Acid and Italicic Acid." *Chem Pharm. Bull.*, Vol. 37, No. 12, pp. 3229–3235 (1989). Isolation of 4 metabolites from bacteria. CA index name, 2-Furanacetic acid, 2,5-dihydro-3-hydroxy-4-(4-methyloctyl)-5-oxo-(9CI); 2-Furanacetic acid, 2,5-dihydro-3-hydroxy-4-(4-methyloctyl)-5-oxo-(9CI); Registry number 126228-72-6.

Wakabayashi, S., "Synthesis of Optically Active Litsenolide C." *The Chemical Society of Japan. Chemistry Letters*

(5) (1987) pp. 875–878. CA index name, 2(5H)-Furanone, 4-hydroxy-5-methyl-3-tetradecyl-(R)-(9CI); Registry number 111722-91-9.

Buck, J. "Directed Metallations of 4-Ethylidenetetronic Acid O-Methyl Ether and its Derivatives as a Synthetic Entry to Natural 4-Oxyfuran-2-ones." *J. Chem. Soc. Perkin Trans 1*, Vol. 11, pp. 2399–2405 (1985).

Vanwagenen, B. S. "Native American Food and Medicinal Plants." *Tetrahedron*, Vol. 42, No. 4, pp. 1117–22. CA index names, 2(5H)-Furanone, 3-hexadecyl-4-hydroxy-5-methyl-(9CI); 2(5H)-Furanone, 3-tetradecyl-4-hydroxy-5-methyl-(9CI).

Chemical Abstracts, Vol. 97: 109463g (1982) Vinyl carbanions. Registry number 82495-62-3 CA index names, 2(5H)-Furanone, 3-(1-hydroxypropyl)-4-methoxy-5-(1-methylethyl)-(9CI).

Anderson, J. R., "Metabolites of Higher Fungi . . . " *J. Chem. Soc., Perkin Trans.* 1, Vol. 1, pp. 215–221. CA index name, 2(5H)-Furanone, 3-ethyl-4-hydroxy- 5-propyl-(9CI). CA registry number 818608-84-6.

Chemical Abstracts, Vol. 87: 184299e (1977). Synthesis of 3,5-didodecyltetronic acid by ozonolysis of 2,6-didodecyl-3,5-dihydroxy-1,4-benzoquinone. Registry number 64580-85-4 CA index name, 2(5H)-Furanone, 3,5-didodecyl-4-hydroxy-(9CI).

Damon, R. E., et al. "A general synthesis of 2-alkyltetronic acids" *Tetrahedron Letters*, Vol. 32, pp. 2749–2752. CA index names, 3-Furanacetic acid, 5-butyl-2,5-dihydro-4-hydroxy-2-oxo, methyl ester (9CI), 2(5H)-Furanone, 4-hydroxy-5-methyl-3-(2-methylpropyl)-(9CI); 2(5H)-Furanone, 3-ethyl-4-hydroxy-5-methyl-(9CI); 2(5H)-Furanone, 4-hydroxy-5-methyl-3-(2-propenyl)-(9CI).

Gudgeon, J. A., et al., "The Structures and Biosynthesis of Multicolanic, Multicolic, and Multicolosic Acis, Novel Tetronic Acid Metabolites of Penicillium Multicolor." *Bioorganic Chemistry*, Vol. 8, pp. 311–322 (1979). CA index name, 2-Furanacetic acid, 2,5-dihydro-3-hydroxy-4-(5-hydroxypentyl)-5-oxo-(9CI).

Gudgeon, J. A., et al., "Use of singly and doubly labeled carbon-13-acetate in the elucidation of the structures and biosynthesis of multicolic and multicolosic acids, new tetronic acids from Penicillium multicolor." *J. Chem. Soc., Chem. Commun.*, Vol. 16, pp. 636–8 (1974). Sudo, R., et al., "Synthesis of Carolic Acid," *J. Org. Chem.*, Vol. 32, No. 6, pp. 1844–6. CA67(5):21426s.

Chemical Abstracts, registry number 6232-63-9, CA index name, 2,4(3H,5H)-Furandione, 3-(2-iminoethyl)-5-methyl-(8CI, 9CI).

Chemical Abstracts, Vol. 63, Column 13064, paragraph "a," (1965), registry number 4697-28-3, CA index name, 2-Furanacetic acid, 4-heptyl-2,5-dihydro-3-hydroxy-.alpha.-(3-methyl-2-butenylidene)-5-oxo-.(9CI).

EP 0,365,329 A2, published Apr. 25, 1990, inventor, Matsumoto, Koichi; et al. Antiobiotics active against Anaerobic Bacteria, their production and use, and strains of Enterobacter producing the same.

EP 0,202,589 A2, published Nov. 26, 1986, inventor, Terao, Shinji; Ascorbic acid derivatives, production and use.

EP 0,480,624 A1, published Apr. 15, 1992, inventor, Treiber, Lazsio; et al., A novel dipeptide isostere inhibits HIV protease.

All the above documents are incorporated by reference herein.

3. Scientific and Historical Background

AIDS is a disease that is characterized by a severe immune deficiency primarily caused by a decreased cell-mediated immune response. Gottlieb, et al., N. Engl. J. Med., 305: 1425–1431 (1981); Masur, et al., N. Engl. J. Med., 305: 1431–1438 (1981). The immunodeficient state is characterized by a decrease in T4 lymphocytes, also known as helper T cells, a reversal of the normal T4<+>:T8<+> cell ratio, lymphopenia, and opportunistic infections often caused by Pneumocystis carinii. Some patients also develop lymphoma or Kaposi's sarcoma at increased incidence. The disease is usually fatal.

The virus that the majority of scientists believes causes AIDS, first identified in 1983, has been described by several names. It is the third known human T-lymphotropic virus (HTLV-III) and has the capacity to replicate within cells of the immune system and thereby lead to a profound destruction of T4<+> T-cells (or CD4<+> cells). See, e.g., Gallo, et al., Science, 224: 500–503 (1984), and Popovic, et al., Science, 224: 497–500 (1984). This retrovirus has been known as lymphadenopathy-associated virus (LAV) or AIDS-related virus (ARV) and, more recently, as human immunodeficiency virus (HIV).

Two distinct AIDS viruses, HIV-1 and HIV-2, have been described. HIV-1 is the virus originally identified in 1983 by Montagnier and co-workers at the Pasteur Institute in Paris. Montagnier, et al., Ann. de Virologie, 135 E: No. 1, 119–134 (1984), while HIV-2 was more recently isolated by Montagnier and his coworkers in 1986. Guyader, Nature, 326: 662–669 (1987). Additional distinct AIDS viruses may exist. As used herein, HIV is meant to refer to all of these viruses in a generic sense.

Retroviruses are enveloped RNA viruses. See, Hayward and Neel, Curr. Top. Microbiol. Immunol., 91: 217–276 (1981). The virus particle consists of a ribonucleoprotein core enclosed by an outer membrane envelope. Viral envelope glycoproteins protrude from the outer envelope. The viral genome consists of two identical single-stranded RNA molecules. Haseltine and Wong-Stall, Scientific American, 259: 52–62 (1988).

U.S. Pat. No. 4,724,232 claims a method of treating humans having AIDS utilizing 3-azido-3-deoxythymidine. On Mar. 20, 1987, the FDA approved the use of this compound, zidovudine (AZT), to treat AIDS patients with a recent initial episode of pneumocystis carinii pneumonia and for treatment of patients infected with the virus with an absolute CD4 lymphocyte count of less than $200/mm^3$ in the peripheral blood. AZT is a known inhibitor of viral reverse transcriptase.

Reverse transcriptase (RT) is an enzyme unique to retroviruses that catalyzes the conversion of viral RNA into double stranded DNA. Blockage at any point during the transcription process, by AZT or any other aberrant deoxynucleoside triphosphate incapable of elongation, is postulated to have dramatic consequences relative to viral replication, although no such therapy has yet been perfected.

Another approach to AIDS therapy focuses on the principal receptor on the T4 cell that the HIV seems to prefer to bind to, the so-called CD4 molecule. This molecule, a nonpolymorphic surface glycoprotein, has been targeted as an intervention point in AIDS therapy. Fisher, et al., Nature, 331: 76–78 (1988); Hussey, et al., Nature, 331: 78–81 (1988); and Deen, et al., Nature, 331: 82–84 (1988).

The present invention concerns a different therapeutic target in AIDS, the inhibition of the viral protease (or proteinase) that is essential for processing HIV-fusion polypeptide precursors. In HIV and several other retroviruses, the proteolytic maturation of the gag (group specific antigen) and gag/pol (polymerase) fusion polypeptides (a process indispensable for generation of infective viral particles) has been shown to be mediated by a protease that is, itself, encoded by the pol region of the viral genome. Yoshinaka, et al., Proc. Natl. Acad. Sci., USA, 82: 1618–1622 (1985); Yoshinaka, et al., J. Virol., 55: 870–873 (1985); Yoshinaka, et al., J. Virol., 57: 826–832 (1986).

The protease (or proteinase) enzyme, consisting of only 99 amino acids, is among the smallest enzyme known. Nutt, et al., Proc. Natl. Acad. Sci., USA, 85: 7129–7133 (1988). Pearl and Taylor, Nature, 329: 351–354 (1987). The three-dimensional structure and mechanism of the enzyme is known. Pearl and Taylor, Nature, 329: 351–354 (1987). Active HIV protease has been expressed in bacteria (e.g., Darke, et al., J. Biol. Chem., 264: 2307–2312 (1989)) and chemically synthesized. Schneider and Kent, Cell, 54: 363–368 (1988); and Nutt, et al., Proc. Natl. Acad. Sci., USA, 85: 7129–7133 (1988). All the above documents are incorporated by reference herein.

This invention comprises novel tetronic acid type compounds that are useful for the inhibition of the HIV protease enzyme. The compounds may be useful for the treatment of a person with AIDS or AIDS related diseases. The compounds may be used in the attempt to retard the further replication of any retrovirus containing the aspartyl protease enzyme or the human retrovirus such as HIV or of treating human cell systems especially including a patient infected with a human retrovirus containing the aspartyl protease enzyme.

SUMMARY OF THE INVENTION

This invention comprises novel compounds. The compounds may be used for the treatment of AIDS. Compositions and formulations including the compounds are also described. Methods for the preparation of a medicament and methods for the treatment of AIDS using the compounds are described. Also described are the procedures for making the compounds. The compounds are represented by the structures shown below,

CHART A

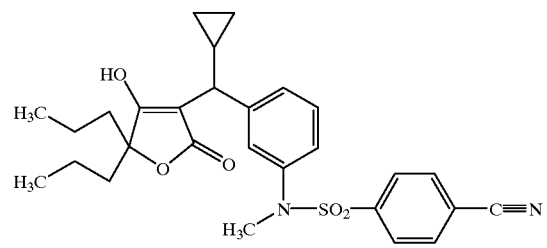

AX-1

CHART B

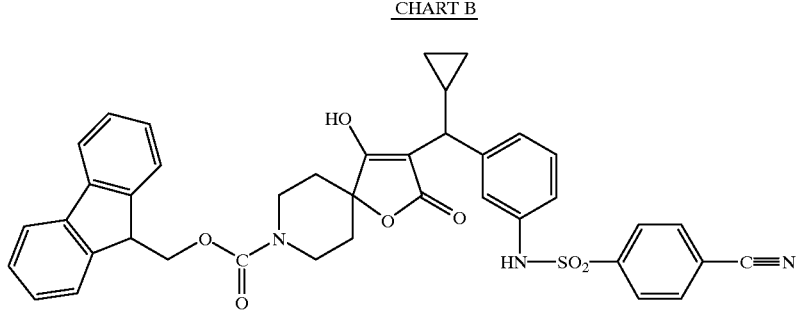

BX-1

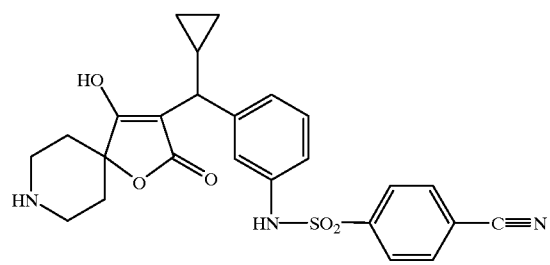

BX-2

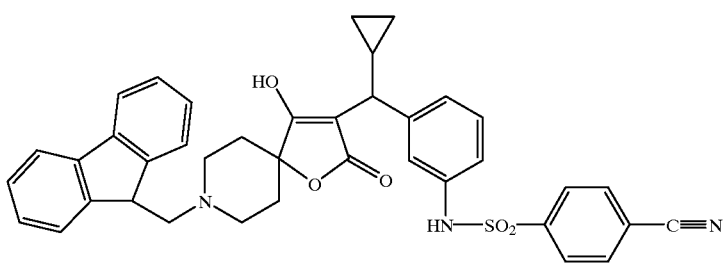

BX-3

BX-4
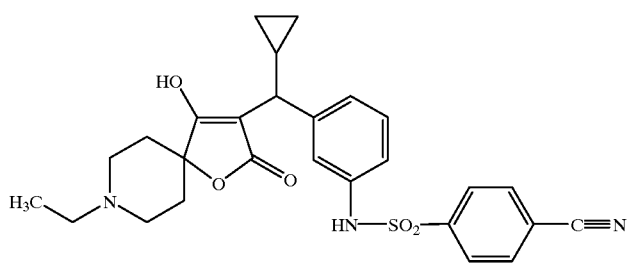
BX-5
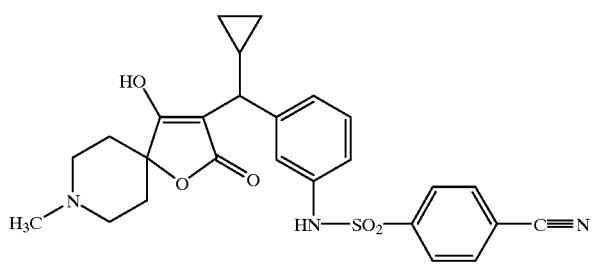
CHART C
CX-1
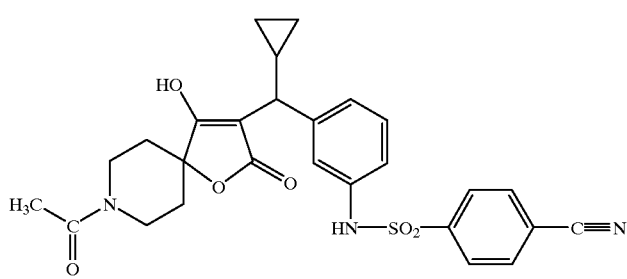
CX-2
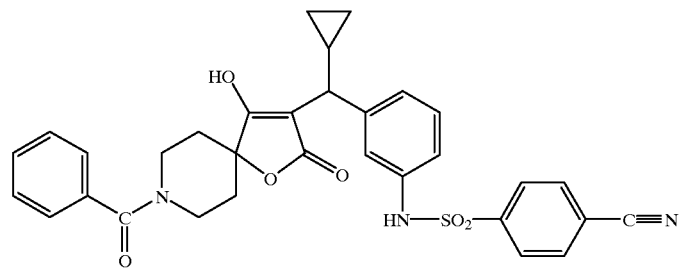
CHART D
DX-1
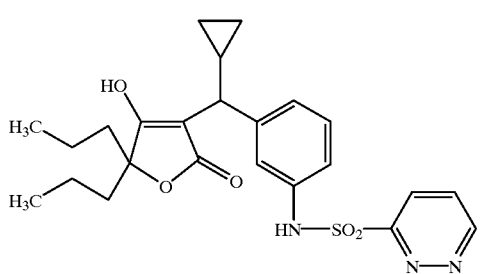
-continued
DX-2
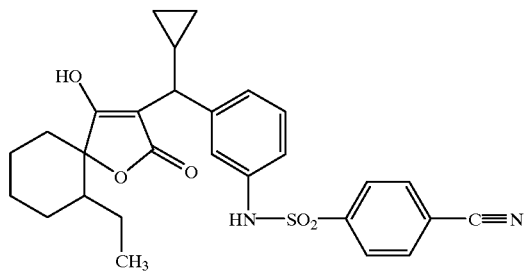

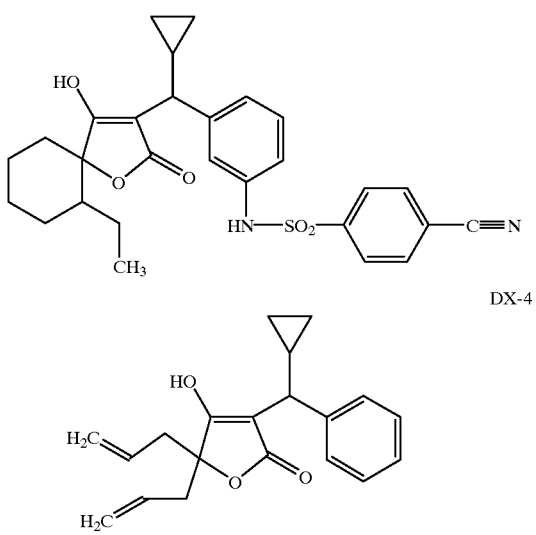

A pharmaceutical composition consisting of a pharmaceutically acceptable carrier and an effective amount of the compounds above. The use of the compounds above to prepare a medicament for treating AIDS and diseases caused by all variants of HIV comprising administering an effective amount of a compounds above to a patient in need thereof. A new compound described by the compounds above and all the variations suggested by the various subgroups described. A new pharmaceutical composition, substantially as herein described. A substance or composition for a new use in a method of treatment, substantially as herein described. A substance or composition for use in a method for treating AIDS or a disease caused by a variant of HIV, said substance or composition comprising the compounds above and said method comprising administering an effective amount of said substance or composition to a patient in need thereof.

ADDITIONAL DESCRIPTION OF THE INVENTION

Definitions

The compounds of this invention are identified in two ways: by descriptive names and by reference to structures having various chemical moieties. The following terms may also be used and are defined below.

OPTIONALLY SUBSTITUTED. The term "optionally substituted" shall mean a group or radical that is substituted with halogen, lower alkyl, mono- or di(lower alkyl)-substituted lower alkyl, (lower alkyl)thio, halo-substituted lower alkyl, amino-substituted lower alkyl, mono- or di(lower alkyl)-substituted amino, lower alkenyl, lower alkynyl, halogen, lower alkoxy, aryloxy, aryl(lower alkyl), hydroxy, cyano, amino, mono- and di(lower alkyl)amino, or nitro and the like.

The parenthetical term $(C_n–C_m)$ or $(C_{n-m})$ is inclusive such that a compound of $(C_1–C_8)$ or $(C_{n-m})$ would include compounds of 0 to 8 carbons and their isomeric forms. The term $C_0$ of would mean no carbon atom or no carbon group in that particular position.

ALKYL. The parenthetical term $(C_n–C_m)$ is inclusive such that a compound of $(C_1–C_8)$ would include compounds of 0 to 8 carbons and their isomeric forms. The various carbon moieties are aliphatic hydrocarbon radicals and includes branched or unbranched forms such as methyl, ethyl, n-propyl, isopropyl, n-butyl, isobutyl, sec-butyl, t-butyl, n-pentyl, isopentyl, n-hexyl, isohexyl, n-heptyl, isoheptyl, and n-octyl and isomeric forms thereof.

LOWER ALKYL. The term "lower alkyl" refers to branched or unbranched saturated hydrocarbon radicals having from one to six carbon atoms. Representatives of such groups are methyl, ethyl, n-propyl, isopropyl, n-butyl, isobutyl, sec-butyl, t-butyl, n-pentyl, isopentyl, hexyl, and the like.

(LOWER ALKYL)THIO. The term "(lower alkyl)thio" refers to a lower alkyl group as defined above, attached to the parent molecular moiety through a sulfur atom. Typical (lower alkyl)thio groups include methylthio, ethylthio, propylthio, isopropylthio, and the like.

ALKOXY. Alkoxy as represented by $—OR_1$ when $R_1$ is $(C_1–C_8)$ alkyl refers to an alkyl radical which is attached to the remainder of the molecule by oxygen and includes branched or unbranched forms such as methoxy, ethoxy, n-propoxy, isopropoxy, n-butoxy, isobutoxy, sec-butoxy, t-butoxy, n-pentoxy, isopentoxy, n-hexoxy, isohexoxy, n-heptoxy, isoheptoxy, and n-octoxy and the like.

LOWER ALKOXY. The term "lower alkoxy" denotes an alkyl group as defined above, attached to the patent molecular moiety through an oxygen atom. Representatives of such groups include methoxy, ethoxy, butyoxy, pentoxy and the like.

ALKENYL. Alkenyl refers to a radical of an aliphatic unsaturated hydrocarbon having at least one double bond and includes both branched and unbranched forms such as ethenyl, (—CH=CH$_2$), 1-methyl-1-ethenyl, 1-propenyl, (—CH$_2$—CH=CH$_2$), 2-propenyl, 1-butenyl, 2-butenyl, 3-butenyl, 2-methyl-1-butenyl, 1-pentenyl, allyl, 3-pentenyl, 4-pentenyl, 1-methyl-4-pentenyl, 3-methyl-1-pentenyl, 3-methyl-allyl, 1-hexenyl, 2-hexenyl, 3-hexenyl, 4-hexenyl, 1-methyl-4-hexenyl, 3-methyl-1-hexenyl, 3-methyl-2-hexenyl, 1-heptenyl, 2-heptenyl, 3-heptenyl, 4-heptenyl, 1-methyl-4-heptenyl, 3-methyl-1-heptenyl, 3-methyl-2-heptenyl, 1-octenyl, 2-octenyl, or 3-octenyl and the like.

ALKYNYL. Alkynyl refers to a monovalent branched or unbranched hydrocarbon radical containing at least one carbon-carbon triple bond, for example ethynyl, propynyl, and the like.

CYCLOALKYL. $(C_3–C_{10})$cycloalkyl refers to a radical of a saturated cyclic hydrocarbon which includes alkyl-substituted cycloalkyl, such as cyclopropyl, 2-methylcyclopropyl, 2,2-dimethylcyclopropyl, 2,3 diethylcyclopropyl, 2-butylcyclopropyl, cyclobutyl, 2-methylcyclobutyl, 3-propylcyclobutyl, cyclopentyl, 2,2-dimethylcyclopentyl, cyclohexyl, cycloheptyl, cyclooctyl and cyclodecyl and the like. Each of these moieties may be substituted as appropriate.

HETEROALKYL. "Heteroalkyl" refers to alkyls as described above, only where one, two or three non-adjacent carbon atoms are replaced by heteroatoms such as nitrogen, sulfur and oxygen.

ARYL. Aryl refers to a 6 to 12 carbon atom base structure, one or two fused or nonfused aromatic rings, that may be optionally substituted or substituted with one to 3 hydroxy, $C_1–C_3$ alkoxy, $C_1–C_3$ alkyl, trifluoromethyl, fluoro, chloro, or bromo groups. Examples of "aryl" are: phenyl, m-methylphenyl, p-trifluoromethylphenyl, α-naphthyl, β-naphthyl, (o-, m-, p-)tolyl, (o-, m-, p-)ethylphenyl, 2-ethyl-tolyl, 4-ethyl-o-tolyl, 5-ethyl-m-tolyl, (o-, m-, or p-)propylphenyl, 2-propyl-(o-, m-, or p-)-tolyl, 4-isopropyl- 2,6-xylyl, 3-propyl-4-ethylphenyl, (2,3,4-, 2,3,6-, or 2,4,5-) trimethylphenyl, (o-, m-, or p-)fluorophenyl, (o-, m-, or p-trifluoromethyl)phenyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5- or 6-)chloro-o-tolyl, 4-chloro-2-propylphenyl, 2-isopropyl-4-chlorophenyl, 4-chloro-3-fluorophenyl, (3- or 4-)chloro-2-fluorophenyl, (o-, m-, or p-)trifluorophenyl, (o-, m-, p-)ethoxyphenyl, (4- or 5-)chloro-2-methoxy-phenyl, and 2,4-dichloro(5- or 6-)methylphenyl and the like. Each of these moieties may be substituted as appropriate.

ALKYLARYL. Alkylaryl refers to alkyl chains of one to 8 carbon atoms and isomeric forms thereof which are substituted with aryl groups of 6 to 12 carbon atoms as described above.

HETEROCYCLICS. Examples of heterocyclics include: (2-, 3-, or 4-)pyridyl, imidazolyl, indolyl, $N^{in}$-formyl-indolyl, $N^{in}$—$C_2$–$C_5$alkyl-C(O)-indolyl, (1,2,4)-triazolyl, (2-, 4-, 5-)pyrimidinyl, (2-, 3-)thienyl, piperidinyl, pyrrolyl, pyrrolinyl, pyrrolidinyl, pyrazolyl, pyrazolinyl, pyrazolidinyl, imidazolyl, imidazolinyl, imidazolidinyl, pyrazinyl, piperazinyl, pyridazinyl, oxazolyl, oxazolidinyl, isoxazolyl, isoxazolidinyl, morpholinyl, thiazolyl, thiazolidinyl, isothiazolyl, isothiazolidinyl, quinolinyl, isoquinolinyl, benzimidazolyl, benzothiazolyl, benzoxazolyl, furyl, puryl, phenazyl, carbazolyl, thienyl, and benzothienyl, thienyl, indolyl, iso-quinolyl and the like. Each of these moieties may be substituted as appropriate.

HETEROARYL or HET. A heteroaryl is a 5- or 6-membered saturated or unsaturated ring containing from one (1) to four (4) heteroatoms selected from the group consisting of nitrogen, oxygen and sulfur; and including any bicyclic group in which any of the above heterocyclic rings is fused to a benzene ring, $C_3$–$C_8$ cycloalkyl, or another heterocycle; and if chemically feasible, the nitrogen and sulfur atoms may be in the oxidized forms; and substituted by zero (0) to three (3) substituents. Substituents attached to either Aryl or Heteroaryl ring systems are denoted with the term "RA."

Examples of heteroaryl can include pyridine, thiophene, furan, pyrimidine, 2-pyridyl, 3-pyridyl, 4-pyridyl, 2-pyrimidinyl, 4-pyrimidinyl, 5-pyrimidinyl, 3-pyridazinyl, 4-pryidazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-indolyl, 3-indolyl, 3-indazolyl, 2-benzoxazolyl, 2-benzothiazolyl, 2-benzimidazolyl, 2-benzofuranyl, 3-benzofuranyl, 2-furanyl, 3-furanyl, 2-thienyl, 3-thienyl, 2-pyrrolyl, 3-pyrrolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 1-purinyl, 3-isothiazolyl, 4-isothiazolyl and 5-isothiazolyl. Each of these moieties may be substituted as appropriate.

AMINO ACIDS. Amino acid residues referred to in this application are listed below, they may also be given either three letter or single letter abbreviations, as follows:

Alanine, Ala, A; Arginine, Arg, R; Asparagine, Asn, N; Aspartic acid, Asp, D; Cystein, Cys, C; Glutamine, Gln, Q; Glutamic Acid, Glu, E; Glycine, Gly, G; Histidine, His, H; Isoleucine, Ile, I; Leucine, Leu, L; Lysine, Lys, K; Methionine, Met, M; Phenylalanine, Phe, F; Proline, Pro, P; Serine, Ser, S; Threonine, Thr, T; Tryptophan, Trp, W; Tyrosine, Tyr, Y; Valine, Val, V; Aspartic acid or Asparagine, Asx, B; Glutamic acid or Glutamine, Glx, Z; Any amino acid, Xaa, X.

All amino acids have a carboxyl group and an amino group. The amino group of the amino acid is also referred to as the "N-terminus" of the amino acid. The carboxyl group of an amino acid is also referred to as the "C-terminus" of the amino acid. The "N-terminus" of an amino acid may form a peptide bond with a carboxyl group of another compound. The carboxyl group that combines with the "N-terminus" of an amino acid may be the carboxyl group of another amino acid or it may be from another source. If several amino acids are linked into a polypeptide, then the polypeptide will have a "free" N-terminus and a "free" C-terminus.

With the compounds of this invention some of the possible moieties are described as "("compound")—C(O)— $RA_{1-3}$" and "("compound")—N(H)$RA_{1-4}$." The groups "$RA_{1-3}$" and "$RA_{1-4}$" (and "$RA_{1-1-3}$" and "$RA_{1-1-4}$") are amino acids of the type listed above. Thus it is understood that $RA_{1-3}$ would be attached to the compound via the "N-terminus" of the amino acid. $RA_{1-3}$ is thus said to be an "N-terminus" amino acid, or even "any N-terminus amino acid," referring to any of the amino acids listed above. $RA_{1-4}$ would be attached to the compound via the "C-terminus" of the amino acid. $RA_{1-4}$ is thus said to be a "C-terminus" amino acid or even "any C-terminus amino acid," referring to any of the amino acids listed above.

It should be apparent then that, compound-C(O)—$RA_{1-3}$ would indicate, compound-C(O)-amino acid, where the N-terminus or amino terminus of the amino acid forms a peptide bond with the compound and compound-N(H)$RA_{1-4}$ would indicate, compound-N(H)-amino acid, where the C-terminus or carboxyl group of the amino acid forms a peptide bond with the compound. The former compound would have a "free" amino or N-terminus and the latter a "free" carboxy or C-terminus.

HALOGEN. The term "halo-" and "halogen" refer to substituents selected from fluoro, chloro, bromo, iodo or trifluoromethyl.

CHIRALITY. It will be apparent to those skilled in the art that compounds of this invention may contain one or more chiral centers and may exist in optically active forms including cis-/trans- and/or R- and S- isomeric forms and mixtures thereof. The scope of this invention includes all of these forms, the enantiomeric or diastereomeric forms of the compounds, including optically active forms, in pure form or as mixtures of enantiomers or diastereomers including cis-/trans-isomeric forms. The therapeutic properties of the compounds may to a greater or lesser degree depend on the stereochemistry of a particular compound.

SALTS. The present invention provides for compounds of formula 1 or pharmacologically acceptable salts and/or hydrates thereof. Pharmacologically acceptable salts refers to those salts that would be readily apparent to a manufacturing pharmaceutical chemist to be equivalent to the parent compound in properties such as formulation, stability, patient acceptance and bioavailability.

The tetronic acids form base addition salts when reacted with bases of sufficient strength. The pharmaceutically acceptable salts include both inorganic and organic bases. The pharmaceutically acceptable salts may be preferred over the free acids since they produce compounds that are more water soluble and more crystalline. The preferred pharmaceutically acceptable salts include, but are not limited to, salts of the mono and divalent metals such as: calcium, lithium, magnesium, potassium, or sodium; and salts formed with organic bases, such as: hydroxide, tro-methamine (THAM), 2-amino-2-(hydroxymethyl)-1,3-propanediol, and other salts as would be apparent to one skilled in the art. Bis salts, where two equivalents of base are added, may also be made from some of the compounds of this invention. Bis salts may be constructed of the salts mentioned above, the following bis salts are frequently used, potassium, or sodium.

Some of the compounds of this invention contain basic functional groups, including amines. These compounds are made into salts when combined with appropriate organic or inorganic acids. These salts can be prepared in situ during the final isolation and purification of the compounds or by separately reacting the purified compound in its free base form with a suitable organic or inorganic acid and isolating the salt thus formed. Representative salts include the acetate, adipates, alginates, aspartates, benzoates, borate, citrate, fumarates, glucoheptonate, hydrochloride, hydrobromide, hydroiodide, lactate, lactiobionate, laurate, malate, maleate, mesylate, naphthylate, nitrate, oleate, oxalate, palmitate, phosphate, propionate, succinate, stearate, sulfate, bisulfate, benzenesulfonates, cyclohexylsulfanates, ethanesulfonates, laurylsulphonate, methanesulfonates, toluenesulfonates, sulfamate, cyclohexylsulfamate, tartrate, tosylate, valerate and other pharmaceutically acceptable counter ions. These salts are readily prepared by methods known in the art.

Additionally, the compounds of this invention may be administered in a suitable hydrated form. Representative alkali or alkaline earth salts include the sodium, potassium, calcium, and magnesium salts and the like. Those skilled in the art would know how to formulate the acids, the salts (including bis salts), and any hydrates of the compounds of this invention into appropriate pharmaceutical dosage forms.

OTHER. LAH is lithium aluminum hydride. LDA is lithium diisopropylamide.

THF is tetrahydrofuran. HRMS is High Resolution Mass Spectrometry, EIMS is electron impact mass spectrometry. Et is ethyl. EOAc is ethyl acetate. HOAc is acetic acid. Carbonyl groups are usually written "C(O)" to indicate a carbon oxygen double bond. Carboxyl is usually written "C(O)O" or "C(O)—O—."

NMR. Operating frequence is $^1$H-NMR (300.133 MHz) and $^{13}$C-NMR (75.469 MHz).

All variables are independently defined unless stated otherwise. For example, if $R_1$ and $R_2$ were both defined as being A, B, or C then $R_1$ could be A at the same time that $R_2$ was A, B or C. When a group can be substituted, usually one to three possibilities, the substitutents need not be the same groups. When a variable in a dependent claim is left undefined it takes the definition of the same variable in the preceding claim from which the dependent claim depends on.

Some variables are combined to form a single recognizable moeity. For example, the $R_2$ and $R_3$ groups may be "combined" to form a cyclic structure. In this situation a $C_6$ cycloalkyl would indicate a six member carbon skelton ring which includes one carbon from the tetronic acid ring. Alternatively, a heterocyclic ring composed of $R_2$ and $R_3$ would be indicated by "—$C_{1-5}$ alkyl-$R_{23}$—$C_{1-5}$ alkyl-." In this latter case, the "—$C_{1-5}$ alkyl-" groups would not include the carbon of the tetronic acid ring, thus a six member hetero ring would be written, "—$C_2$ alkyl-$R_{23}$—$C_2$ alkyl-." Note that there does not have to be an equal number of carbon atoms on either side of the $R_{23}$ group, nor does $R_{23}$ have to be a hetero atom.

Administration and Compositions

In clinical practice the compounds of the present invention will normally be administered orally, rectally, or by injection, in the form of pharmaceutical preparations comprising the active ingredient either as a free acid or as a pharmaceutically acceptable non-toxic, base addition salt, such as of the types listed above in association with a pharmaceutically acceptable carrier. The use and administration to a patient to be treated in the clinic would be readily apparent to a physician or pharmacist or ordinary skill in the art.

The present invention also provides pharmaceutical compositions which comprise one or more of the compounds of formula I above formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally (i.e., intravenously, intramuscularly, or subcutaneously), intracisternally, intravaginally, intraperitoneally, topically (as by powders, ointments, or drops), bucally, or as an oral or nasal spray.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

If desired and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a)

fillers or extenders such as starches, lactose, sucrose, glucose, mannitol, and silicic acid, b) binders such as, for example, carboxymethylcellulose, alignates, gelatin, polyvinylpyrrolidone, sucrose, and acacia, c) humectants such as glycerol, d) disintegrating agents such as agar—agar, calcium carbonate, potato ortapioca starch, alginic acid, certain silicates, and sodium carbonate, e) solution retarding agents such as paraffin, f) absorption accelerators such as quaternaryammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in sort and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite agar—agar, and tragacanth, and mixtures thereof.

Compositions for rectal or vaginal administration are preferably suppositories which can be prepared by mixing the compounds of this invention with suitable nonirritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Ophthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. Generally dosage levels of about 0.1 to about 200, more preferably of about 0.5 to about 150, and most preferably about 1 to about 125 mg of active compound per kilogram of body weight per day are administered orally to a mammalian patient. If desired, the effective daily dose may be divided into multiple doses for purposes of administration, e.g., two to four separate doses per day.

Utility of the Invention

The compounds of formula I of the present invention inhibit retroviral proteinases, having a aspartyl protease enzyme, and thus inhibit the replication of the virus. More particularly, the compounds of the present invention are useful as novel human retroviral protease inhibitors, having a aspartyl protease enzyme. They are useful for treating human patients infected with a human retrovirus containing the aspartyl protease enzyme, such as human immunodeficiency virus (strains of HIV-1 or HIV-2) or human T-cell leukemia viruses (HTLV-I or HTLV-II) which results in acquired immunodeficiency syndrome (AIDS) and/or related diseases.

The capsid and replicative enzymes (i.e. protease, reverse transcriptase, integrase) of retroviruses are translated from the viral gag and pol genes as polyproteins that are further processed by the viral protease (PR) to the mature proteins found in the viral capsid and necessary for viral functions and replication. If the PR is absent or nonfunctional, the virus cannot replicate. The retroviral PR, such as HIV-1 PR or HIV-2 PR has been found to be an aspartic protease with active site characteristics similar to those exhibited by the more complex aspartic protease, renin.

The term human retrovirus (HRV) includes human immunodeficiency virus type I, human immunodeficiency virus type II, or strains thereof, as well as human T cell leukemia virus 1 and 2 (HTLV-1 and HTLV-2) or strains apparent to one skilled in the art, which belong to the same or related viral families and which create similar physiological effects in humans as various human retroviruses containing the aspartyl protease enzyme.

More specifically, an example of one such human retrovirus containing the aspartyl protease enzyme is the human immunodeficiency virus (HIV, also known as HTLV-III or LAV) which has been recognized as the causative agent in human acquired immunodeficiency syndrome (AIDS). HIV contains a retro viral encoded protease, HIV-I protease, that cleaves the fusion polypeptides into the functional proteins of the mature viral particle, E. P. Lillehoj, et al., J. Virology, 62:3053 (1988); C. Debuck, et al., Proc. Natl. Acad. Sci., 84:8903 (1987). This enzyme, HIV-I protease, has been classified as an aspartyl protease and has a demonstrated homology to other aspartyl proteases such as renin, L. H. Pearl, et al., Nature 329:351 (1987); I. Katoh, et al., Nature 329:654 (1987). Inhibition of HIV-I protease blocks the replication of HIV and thus is useful in the treatment of human AIDS, E. D. Clerq, J. Med. Chem. 29:1561 (1986). Inhibitors of HIV-I protease are useful in the treatment of HIV-infected individuals who are asymptomatic or symptomatic of AIDS.

Pepstatin A, a general inhibitor of aspartyl proteases, has been disclosed as an inhibitor of HIV-I protease, S. Seelmeier, et al., Proc. Natl. Acad. Sci. USA, 85:6612 (1986). Other substrate derived inhibitors containing reduced bond isosteres or statine at the scissle position have also been disclosed, M. L. Moore, et al., Biochem. Biophys, Res. Commun. 159:420 (1989); S. Billich, et al., J. Biol. Chem. 263:17905 (1988); Sandoz, D. E. 3812-576-A.

Patients to be treated would be those individuals: 1) infected with one or more strains of a human retrovirus containing the aspartyl protease enzyme as determined by the presence of either measurable viral antibody or antigen in the serum and 2) in the case of HIV, having either an asymptomatic HIV infection or a symptomatic AIDS defining infection such as i) disseminated histoplasmosis, ii) isopsoriasis, iii) bronchial and pulmonary candidiasis including pneumocystic pneumonia iv) non-Hodgkin's lymphoma or v) Kaposi's sarcoma and being less than sixty years old; or having an absolute CD4+ lymphocyte count of less than 500/mm$^3$ in the peripheral blood. Treatment would consist of maintaining an inhibitory level of the compound used according to this invention in the patient at all times and would continue until the occurrence of a second symptomatic AIDS defining infection indicates alternate therapy is needed.

Thus, the compounds of the present invention are useful for treating diseases caused by retroviruses containing the aspartyl protease enzyme, such as human acquired immunodeficiency disease syndrome (AIDS).

The compounds are also useful for treating non-human animals infected with a retrovirus containing the aspartyl protease enzyme, such as cats infected with feline leukemia virus or feline immunodeficiency virus, simians infected with the simian immunodeficiency virus, goats, and any other animal that may be infected with a virus containing the aspartyl protease enzyme. Exact dosages, forms and modes of administration of the compounds of the present invention to non-human animals would be apparent to one of ordinary skill in the art, such as a veterinarian.

The compounds of formula I of the present invention are prepared as described in the Preparations and Examples below, or are prepared by methods analogous thereto, which are readily known and available to one of ordinary skill in the art of organic synthesis.

Also claimed are essential intermediates, useful in the preparation of the compounds of formula 1.

Measures of Activity

The HIV protease assay. Surprisingly and unexpectedly, the compounds of the present invention are effective and potent inhibitors of HIV protease. The HIV protease assay is described below.

Because the compounds of the present invention inhibit retroviral proteases, having an aspartyl protease enzyme, they are expected to inhibit the replication of the HIV virus. The compounds are thus useful for treating human patients infected with a human retrovirus containing the aspartyl protease enzyme, such as human immunodeficiency virus (strains of HIV-1 or HIV-2) or human T-cell leukemia viruses (HTLV-I or HTLV-II) that results in acquired immunodeficiency syndrome (AIDS) and/or related diseases.

The term human retrovirus (HRV) includes human immunodeficiency virus type I, human immunodeficiency virus type II, or strains thereof, as well as human T cell leukemia virus 1 and 2 (HTLV-1 and HTLV-2) or strains apparent to one skilled in the art, that belong to the same or related viral families and that create similar physiological effects in humans as various human retroviruses containing the aspartyl protease enzyme.

Patients to be treated are those individuals: 1) infected with one or more strains of a human retrovirus containing the aspartyl protease enzyme as determined by the presence of either measurable viral antibody or antigen in the serum and 2) in the case of HIV, having either a symptomatic AIDS defining infection such as i) disseminated histoplasmosis, ii) isopsoriasis, iii) bronchial and pulmonary candidiasis including pneumocystic pneumonia, iv) non-Hodgkin's lymphoma or v) Kaposi's sarcoma. Treatment consists of maintaining an inhibitory level of the compound used according to this invention in the patient at all times and would continue until the occurrence of a second symptomatic AIDS defining infection indicates alternate therapy is needed.

More specifically, an example of one such human retrovirus is the human immunodeficiency virus (HIV, also known as HTLV-III or LAV) that has been recognized as the causative agent in human acquired immunodeficiency disease syndrome (AIDS), Gallo, et al., Science, 224: 500–503 (1984). HIV contains a retro viral encoded protease, HIV-I protease, that cleaves the fusion polypeptides into the functional proteins of the mature virus particle. Lillehoj, et al., J. Virology, 62: 3053–3058 (1988); Debouck, et al., Proc. Natl. Acad. Sci., USA, 84: 8903–8906 (1987). This enzyme, HIV-I protease, has been classified as an aspartyl protease and has a demonstrated homology to other aspartyl proteases such as renin. Pearl and Taylor, Nature, 329: 351–354 (1987); Katoh, et al., Nature, 329: 654–656 (1987). Inhibition of HIV-I protease blocks the replication of HIV and thus is useful in the treatment of human AIDS. Clercq, J. Med. Chem., 29: 1561–1569 (1986). Inhibitors of HIV-I or HIV-II protease are useful in the treatment of AIDS.

IN VITRO HIV PROTEASE INHIBITORY ASSAY

The HIV protease screening assay is based on a fluorescently labeled substrate which can be resolved from nonlabeled cleavage product using avidin-polystyrene particles, 0.7–0.9 μm. The substrate is biotinylated at the amino terminal arginine and fluorescently labeled with fluorescein isothiocynate (FITC) at the carboxyl terminal lysine. This assay has been employed to detect novel, nonpeptidic inhibitors of HIV-1 protease. Substrate (20 μl of 0.2 μM), sample (10 μl of desired concentration), and enzyme (10 μl of 0.1 μM) are added to a 96 well pandex plate. The assay is run in 0.1 M sodium acetate buffer at pH 5.5 in the presence of 1.0 M sodium chloride and 0.05% NP-40 and incubated in the dark for one hour at room temperature. Avidin coated polystyrene beads (40 μl of 0.1% (w/v)) are added and the incubation is continued in the dark for an additional half hour. The labeled cleavage product is separated from the unreacted substrate via filtration and is read on the IDEXX Screen Machine. (IDEXX Corporation—Portland, Maine) The data are analyzed by appropriate computer algorithms to ascertain percent inhibition values.

The Activity Table showing the results of the HIV Protease Inhibitory Assay appears below in TABLE 1. The table has three columns, the left column provides the code number of the compound for easy cross reference to structure tables and detailed procedures, the middle column provides the concentration of test compound and the column on the right provides the percent inhibition.

Determination of $K_i$ values utilizes the same materials and equipment employed for percent inhibition studies. Two-fold serial dilutions are made for a given inhibitor from 2, 3 or 4 starting concentrations with a total of 24, 36 or 48 individual inhibitor concentrations. These dilutions are performed utilizing the BioMek robotics system. The assay consists of 10 μL of 40 nM HIV-1 protease, 10 μL of the various inhibitor concentrations, and 20 μL of 200 μM substrate (40 uL total). The reaction is allowed to proceed for 90 min at room temperature, terminated with 40 μL of avidin beads and processed (supra vide). An inhibitor with a known $K_i$ is run in parallel to verify the validity of the assay. The data is processed utilizing a computer program employing a nonlinear least square analysis of the data to generate the $K_i$ values.

The % inhibition values and, in some instances, $IC_{50}$ values or $K_i$ values, of representative compounds of the present invention are listed in Tables II and IV below.

Several compounds of the present invention, such as IX-14, IX-17 and IX-24 were tested in known human cell lines, such as human T-cell lines, e.g., MT4 and H9, which were infected with HIV-$1_{IIIB}$, and were found to inhibit retroviral replication.

Preparation of the Compounds

The compounds of this invention may be prepared according to the instructions provided below or by reference to the published patent application numbered PCT/US94/09533, filed Sep. 7, 1994, incorporated by reference herein.

The compounds of the present invention are also prepared as described in the Charts, Preparations and Examples below, or are prepared by methods analogous thereto, which are readily known and available to one of ordinary skill in the art of organic synthesis. Specific references to delineated sections of PCT/US94/09533 are made below.

The descriptions below refer to the various CHARTS which show figures and formula that represent various compounds. The structures, or formula, are provided to facilitate an understanding of the description of the invention. The structures in the CHARTS provide general descriptions of reaction schemes and are not intended to limit the procedures to describe only those compounds shown. The aromatic structures in the figures indicate not only benzene but any suitable aromatic group, including obvious substitutions, such as those provided in the definition section for aryl, heteroaryl and the like.

In addition to the preparations and procedures below many of the side chains to the basic tetronic acid "core" structure will be apparent to one ordinarily skilled in the art. Tetronic acid is the trivial name for 5H-Furan-2-one,4-hydroxy. Additional side chains are disclosed in WO 94/11361, published May 26, 1994, (International Application No. PCT/US93/10645) and WO 94/18188, published Aug. 18, 1994, (International Application No. PCT/US94/00938), incorporated by reference herein. Reference to those documents may be necessary for a complete description of how to make some of the compounds described in this invention.

CHART A

Chart A describes a method for preparing N-methyl sulfonamides of general formula A-4. This method is a alternative to the method described in Chart M of PCT/US94/09533. Reaction of N—Z protected compounds of general structure I-9 (prepared as described in Chart I of PCT/US94/09533) with lithium aluminum hydride provides the N-methyl analog of structure A-1 (for the preparation of N-methyl compounds by the action of lithium aluminum hydride on N—Z protected carbamates see: Weiss, B. *J. Org. Chem.* 1965, 30, 2483). Reaction of the intermediate with an excess of sulfonyl chloride (A-2) affords the bis-sulfonyl analog of general structure A-3. The sulfate is selectively hydrolyzed with potassium carbonate in aqueous ethanol to afford the N-methyl sulfonamide of general structure A-4.

Preparation AP-1

Chart A, "A-3" Where $R_2$ and $R_3$ are Propyl, $Z_5$ is Cyclopropyl and $Z_8$ is 4-cyanophenyl To a solution of IX-32 (Chart I of PCT/US94/09533) (225 mg, 0.48 mmol) in anhydrous THF (16 mL) was added lithium aluminum hydride (0.60 mL of a 1.0 M solution in THF, 0.60 mmol). The reaction mixture was stirred overnight and poured into cold (0–5° C.) ethyl acetate (10 mL). The resulting thick suspension was stirred for 10 minutes at 0–5° C., allowed to warm to room temperature and stirred an additional 10 minutes. 2-Propanol (10 mL) was added and the reaction mixture concentrated in vacuo. The crude product was used without purification.

To a cooled (0–5° C.) solution of the solid obtained above in anhydrous methylene chloride (16 mL) and anhydrous DMF (4 mL) was added triethylamine (121 mg, 0.167 mL, 1.2 mmol) and 4-cyanobenzene sulfonyl chloride (242 mg, 1.2 mmol). The reaction mixture was stirred for 1 hour at 0–5° C., allowed to warm to room temperature and stirred overnight. Additional triethylamine (24 mg, 0.033 mL, 0.24 mmol) and 4-cyanobenzene sulfonyl chloride (48 mg, 0.24 mmol) were added and the reaction mixture stirred 4 hours at room temperature. Volatiles were removed in vacuo and the residue partitioned between ethyl acetate and 0.25 N aqueous HCl. The organic layer was washed with 0.25 N HCl and brine, dried ($MgSO_4$), filtered and concentrated in vacuo. Purification of the residue by flash chromatography using methylene chloride/ethyl acetate/hexane (1:1:4) as eluent afforded the bis sulfonyl compound of general formula A-3 (182 mg, 56%) as a solid: $^1$H NMR ($CDCl_3$) δ 8.11 (d, J=8.6 Hz, 2H), 7.97 (d, J=8.6 Hz, 2H), 7.76 (d, J=8.5 Hz, 2H), 7.65 (d, J=8.6 Hz, 2H), 7.50 (d, J=7.9 Hz, 1H), 7.31 (t, J=7.9 Hz, 1H), 7.13–7.05 (m, 2H), 3.19–3.16 (overlapping m, 4H), 1.78–1.46 (m, 5H), 1.33–1.12 (m, 4H), 0.90 (t, J=7.2 Hz, 3H), 0.82 (t, J=7.2 Hz, 3H), 0.72–0.69 (m, 1H), 0.58–0.55 (m, 1H), 0.29–0.27 (m, 2H) ppm; 13C NMR ($CDCl_3$) δ 168.83, 163.81, 141.41, 140.66, 139.43, 133.58, 132.69, 129.11, 128.39, 127.22, 125.35, 122.39, 119.11, 177.41, 116.49, 116.31, 86.59, 45.43, 38.11, 37.80, 37.67, 15.86, 13.89, 13.22, 6.62, 3.99 ppm; EIMS m/z 674 (M+H$^+$).

Preparation AP-2 and Example AX-1

Chart A, "A-4" Where $R_2$ and $R_3$ are Propyl, $Z_5$ is Cyclopropyl and $Z_8$ is 4-cyanophenyl To a suspension of the bis sulfonyl compound of general structure A-3 described above (182 mg, 0.27 mmol) in 50% aqueous ethanol (10 mL) was added potassium carbonate (45 mg, 0.32 mmol). The mixture was heated to gentle reflux causing complete dissolution. After one hour at reflux the solution was cooled to room temperature and stirred overnight. The mixture was partially concentrated in vacuo and partitioned between chloroform and 0.25 N HCl. The organic layer was washed with 0.25 N HCl and brine, dried ($MgSO_4$), filtered and concentrated in vacuo. Purification of the residue by flash chromatography using methylene chloride/ethyl acetate/hexane (1:1:4) as eluent afforded the N-methyl sulfonamide of general structure A-4 (80 mg, 58%) as a solid: $^1$H NMR (CDCl$_3$) δ 7.75 (d, J=6.8 Hz, 2H), 7.63 (d, J=6.8 Hz, 2H), 7.30–7.19 (m, 3H), 6.88 (d, J=7.8 Hz, 1H), 3.15 (s, 3H), 3.06 (d, J=9.5 Hz, 1H), 1.76–1.71 (m, 4H), 1.44–1.40 (m, 1H), 1.25–1.10 (m, 4H), 0.93–0.80 (m, 6H), 0.68–0.53 (m, 2H), 0.24–0.17 (m, 2H) ppm; 13C NMR (CDCl$_3$) δ 176.32, 174.87, 143.59, 140.63, 132.68, 129.11, 128.39, 127.41, 125.69, 124.37, 117.27, 116.35, 104.83, 86.62, 43.40, 38.11, 16.02, 13.98, 13.57, 5.55, 4.10 ppm; EIMS m/z 508 (M$^+$).

CHART B

Chart B describes a method for preparing N-alkyl azaspiro tetronic acids of general structure B-5. Removal of the 9-fluorenylmethyloxycarbonyl protecting group of intermediate B-1 (prepared according to Chart I of PCT/US94/09533) provides the amine of general structure B-2 along with variable amounts of byproduct of general structure B-3. Reductive alkylation with aldehydes of general structure B-4 provides the N-alkyl products of general structure B-5.

Example BX-1
Chart B, "B-1" Where $Z_5$ is Cyclopropyl and $Z_6$ is 4-cyanophenyl The title compound was prepared according to Chart I of PCT/US94/09533 using the product of preparation PP-3 as the tetronic acid intermediate of general structure C-5.

Physical characteristics are as follows: $^1$H NMR (CDCl$_3$) δ 7.84 (d, J=6.9 Hz, 2H), 7.80 (d, J=11.8 Hz, 2H), 7.73 (d, J=15.1 Hz, 2H), 7.55 (d, J=7.4 Hz, 2H), 7.40 (t, J=6.9 Hz, 2H), 7.34–7.28 (m, 2H), 7.18–7.09 (m, 3H), 6.89–6.86 (m, 1H), 4.41 (br, 2H), 4.24 (t, J=6.7 Hz, 1H), 4.13 (br, 2H), 3.20 (br, 3H), 2.84 (d, J=10.1 Hz, 1H), 2.05–1.94 (m, 2H), 1.57–1.48 (m, 3H), 0.56–0.51 (m, 2H), 0.16–0.14 (m, 2H) ppm; $^{13}$C NMR (CDCl$_3$) δ 177.40, 172.98, 155.31, 144.30, 143.55, 143.30, 141.08, 135.87, 132.50, 128.99, 127.59, 126.89, 124.80, 124.62, 120.96, 119.85, 119.51, 117.14, 115.90, 102.31, 79.77, 67.51, 53.25, 46.96, 43.59, 40.09, 13.29, 5.63, 4.18 ppm; MS (FAB) m/z 702 (M$_+$H$^+$).

Preparation BP-1 and Example BX-2
Chart B, "B-2" Where $Z_5$ is Cyclopropyl and $Z_6$ is 4-cyanophenyl To a solution of BX-1 (150 mg, 0.21 mmol) in anhydrous dimethylformamide (3 mL) at room temperature was added diethylamine (0.22 mL, 2.14 mmol). The resulting solution was stirred for 2 h and volatiles removed in vacuo. The resulting residue was triturated with diethyl ether, filtered and washed several times with diethyl ether to afford a crude mixture containing the desired product along with variable amounts of the byproduct of general structure B-3. This mixture was typically used without further purification, however, pure BX-2 was obtained by purification by reverse-phase flash chromatography using 40 μm C-18 reverse phase silica gel and eluting with 30% aqueous acetonitrile as eluant to afford the title compound (13 mg, 13%) as a white solid: $^1$H NMR (CDCl$_3$) δ 7.87 (d, J=8.5 Hz, 2H), 7.70 (d, J=8.5 Hz, 2H), 7.23 (d, J=7.8 Hz, 1H), 7.13–7.08 (m, 2H), 6.91 (d, J=7.9 Hz, 1H), 3.61–3.19 (m, 4H), 2.68 (d, J=10.0 Hz, 1H), 2.31–2.13 (m, 2H), 1.75–1.48 (m, 3H), 0.55–0.37 (m, 2H), 0.22–0.03 (m, 2H) ppm; MS (EI) m/z 479.

Preparation BP-2 and Example BX-3
Chart B, "B-3" Where $Z_5$ is Cyclopropyl and $Z_6$ is 4-cyanophenyl and

Example BX-4
Chart B, "B-5" Where $Z_5$ is Cyclopropyl, $Z_6$ is 4-cyanophenyl and $Z_9$ is Methyl To a suspension of the crude product from preparation BP-1 (128 mg, 0.27 mmol) in anhydrous tetrahydrofuran (3 mL) at room temperature was added sodium triacetoxyborohydride (86 mg, 0.41 mmol), acetaldehyde (general structure B-4 where $Z_9$ is methyl) (0.075 mL, 1.34 mmol) followed by glacial acetic acid (0.016 mL, 0.27 mmol). The solution was stirred at for 18 h and volatiles removed in vacuo. The residue was purified by flash chromatography eluting with methylene chloride/methanol (5%) to afford BX-3 (23 mg, 13%) as a brown solid and BX-4 (34 mg, 25%) as a light brown solid.

Physical characteristics of BX-3 are as follows: $^1$H NMR (CDCl$_3$) δ 7.86–7.79 (m, 4H), 7.71–7.63 (m, 4H), 7.47–7.38 (m, 4H), 7.21–7.09 (m, 3H), 6.96–6.93 (m, 1H), 4.31–4.22 (m, 1H), 3.38–3.35 (m, 2H), 3.18–2.85 (m, 3H), 2.71 (d, J=10.1 Hz, 1H), 2.35–2.16 (m, 2H), 1.70–1.53 (m, 3H), 0.55–0.40 (m, 2H), 0.21–0.03 (m, 2H) ppm; MS (FAB) m/z (M+H) 658.

Physical characteristics of BX-4 are as follows: $^1$H NMR (CDCl$_3$) δ 7.86 (d, J=6.9 Hz, 2H), 7.71 (d, J=8.6 Hz, 2H), 7.24 (d, J=7.7 Hz, 1H), 7.1 (d, J=7.8 Hz, 2H), 6.93 (d, J=7.9 Hz, 1H), 3.97 (br, 2H), 3.48–3.33 (m, 2H), 3.24–3.05 (m, 4H), 2.70 (d, J=10.0 Hz, 1H), 2.44–2.24 (m, 2H), 1.80–1.52 (m, 3H), 1.36 (t, J=7.3 Hz, 3H), 0.47–0.41 (m, 2H), 0.19–0.07 (m, 2H) ppm; $^{13}$C NMR (CDCl$_3$) δ 177.79, 147.34, 143.71, 135.91, 132.59, 128.65, 127.81, 124.79, 120.89, 118.69, 117.46, 115.68, 94.05, 91.88, 52.53, 51.91, 43.79, 30.11, 14.05, 9.30, 5.75, 4.35 ppm; MS (EI) m/z 507.

Example BX-5
Chart B, "B-5" Where $Z_5$ is Cyclopropyl, $Z_6$ is 4-cyanophenyl and $Z_9$ is Proton Physical characteristics are as follows: $^1$H NMR (CDCl$_3$) δ 7.86 (d, J=8.6 Hz, 2H), 7.71 (d, J=8.5 Hz, 2H), 7.25 (d, J=8.6 Hz, 1H), 7.13–7.07 (m, 2H), 6.91 (d, J=7.9 Hz, 1H), 3.62 (br, 2H), 3.40–3.16 (m, 4H), 2.81–2.55 (m, 4H), 2.41–2.23 (m, 2H), 1.78–1.50 (m, 3H), 0.68–0.49 (m, 2H), 0.25–0.06 (m, 2H) ppm; $^{13}$C NMR (CDCl$_3$) δ 177.85, 147.23, 143.57, 135.85, 132.50, 128.62, 127.69, 124.65, 120.65, 118.15, 117.33, 115.66, 93.81, 51.22, 43.69, 43.23, 30.18, 14.07, 5.73, 4.19 ppm; MS (EI) m/z 493.

CHART C

Chart C describes a method for preparing N-acyl azaspirotetronic acids of general structure C-3. Removal of the 9-fluorenylmethyloxycarbonyl protecting group followed by acylation with an acid chloride of general structure C-1 or anhydride of general structure C-2 provides the acyl derivatives of general structure C-3.

Preparation CP-1 and Example CX-1
Chart C, "C-3" Where $Z_5$ is Cyclopropyl, $Z_6$ is 4-cyanophenyl and $Z_{10}$ is Methyl To a solution of BX-1 (100 mg, 0.14 mmol) in anhydrous dimethylformamide (3 mL) at room temperature was added diethylamine (0.2 mL). The resulting solution was stirred for 90 minutes and volatiles removed in vacuo.

To a cooled (0–5° C.) solution of the residue obtained above in anhydrous methylene chloride (4 mL) and dimethylformamide (1 mL) was added acetic anhydride (14.5 μL, 0.15 mmol). The solution was stirred for 90 minutes at 0–5° C. and volatiles removed in vacuo. The residue was purified by semi-preparative HPLC (24.5×250 mm Vydac C-18 column) eluting with aqueous acetonitrile as eluent to afford the title compound (31 mg, 42%) as a solid: $^{13}$C NMR (CDCl$_3$) δ 176.61, 172.71, 169.94, 144.36, 143.37, 135.96, 132.57, 129.13, 127.74, 124.91, 120.98, 119.65, 117.27, 116.02, 103.04, 79.65, 43.83, 42.98, 38.19, 33.59, 31.93, 29.58, 20.98, 13.36, 5.71, 4.32 ppm; MS (EI) m/z 521.

Example CX-2

Chart C, "C-3" Where Z$_5$ is Cyclopropyl, Z$_6$ is 4-cyanophenyl and Z$_{10}$ is Phenyl Physical characteristics are as follows: $^{13}$C NMR (CDCl$_3$) δ 176.69, 172.76, 171.22, 144.25, 143.42, 136.03, 134.89, 132.56, 130.09, 129.04, 128.59, 127.67, 126.55, 124.75, 120.93, 119.56, 117.25, 115.92, 102.94, 79.78, 44.15, 43.76, 38.72, 32.98, 32.58, 29.22, 13.33, 5.70, 4.22 ppm.

CHART D

The following compounds were prepared as described in Chart I of PCT/US94/09533.

Example DX-1

Chart I of PCT/US94/09533 "I-8" Where R$_2$ and R$_3$ are Propyl, Z$_5$ is Cyclopropyl and Z$_6$ is 3-pyridazinyl Physical characteristics are as follows: $^1$H NMR (CDCl$_3$) δ 9.26–9.24 (m, 1H), 8.04 (d, J=8.5 Hz, 1H), 7.73–7.68 (m, 1H), 7.28 (s, 1H), 7.18–6.97 (m, 3H), 3.81 (br, 1H), 2.84 (d, J=10.1 Hz, 1H), 1.78–1.51 (m, 5H), 1.29–1.07 (m, 4H), 0.89–0.81 (m, 6H), 0.60–0.45 (m, 2H), 0.18–0.09 (m, 2H) ppm; $^{13}$C NMR (CDCl$_3$) δ 176.10, 174.41, 161.07, 152.78, 144.38, 135.27, 128.82, 128.44, 126.33, 124.99, 121.48, 120.09, 104.19, 85.67, 43.65, 37.88, 37.70, 15.75, 13.76, 13.45, 5.75, 3.91 ppm; MS (EI) m/z 471.

Example DX-2

Chart I of PCT/US94/09533 "I-8" Where R$_2$ and R$_3$ Together Represent a 2-(ethyl)cyclohexyl Ring, Z$_5$ is Cyclopropyl and Z$_6$ is 4-cyanophenyl The title compound and example DX-3 were prepared as described in Chart I of PCT/US94/09533 from 2-ethylcyclohexanone which was prepared as described in Chart L of PCT/US94/09533.

Physical characteristics of CX-2 are as follows: MS (EI) m/z 506.

Example DX-3

Chart I of PCT/US94/09533 "I-8" Where R$_2$ and R$_3$ Together Represent a 2-(ethyl)cyclohexyl Ring, Z$_5$ is Cyclopropyl and Z$_6$ is 4-cyanophenyl Physical characteristics of CX-2 are as follows: MS (EI) m/z 506.

The following compound was prepared according to Chart D of PCT/US94/09533.

Example DX4

Chart D of PCT/US94/09533 "D-2" Where R$_2$ and R$_3$ are Allyl

Physical characteristics of CX-2 are as follows: MS (EI) m/z 310.

Table of Structures

CHART A

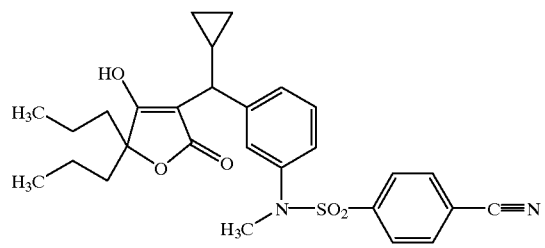

AX-1

CHART B

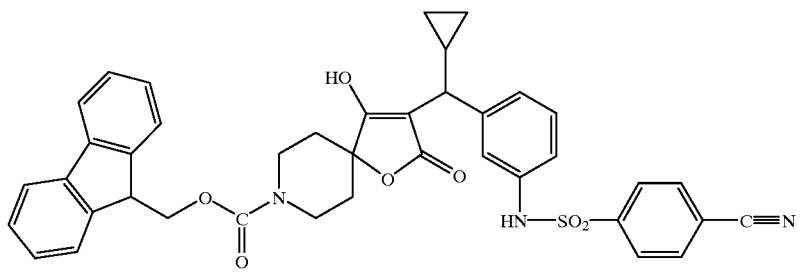

BX-1

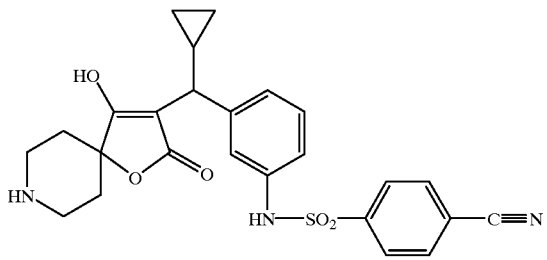

BX-2

-continued
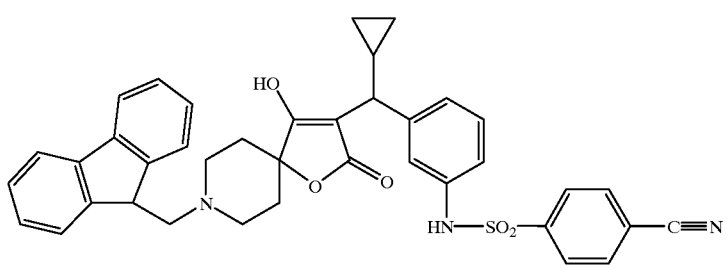
BX-3
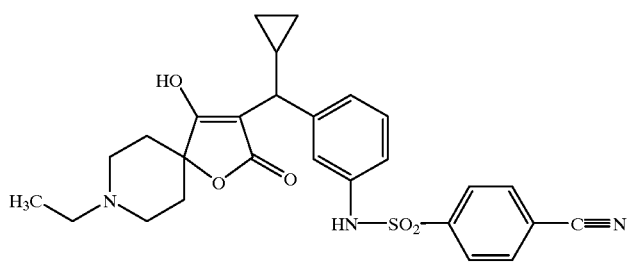
BX-4
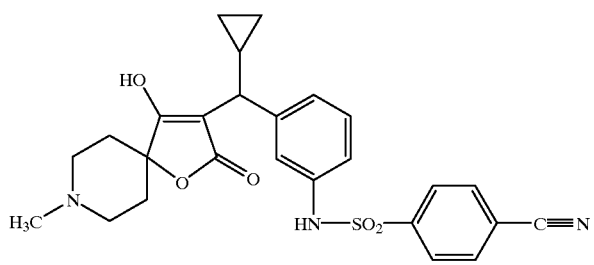
BX-5
CHART C
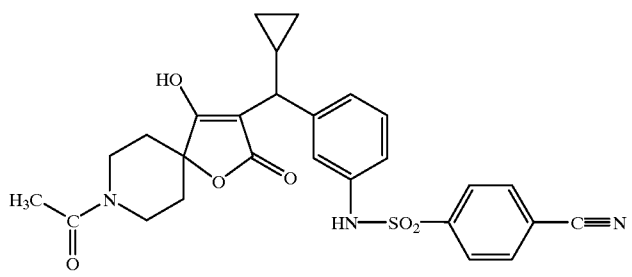
CX-1
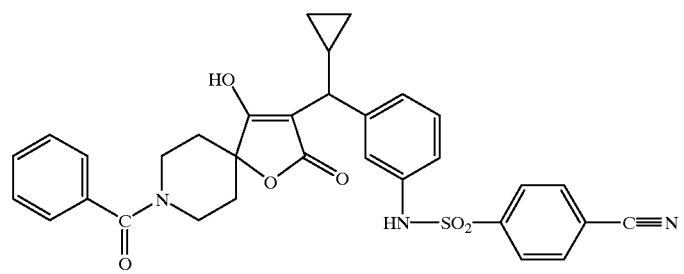
CX-2

CHART D
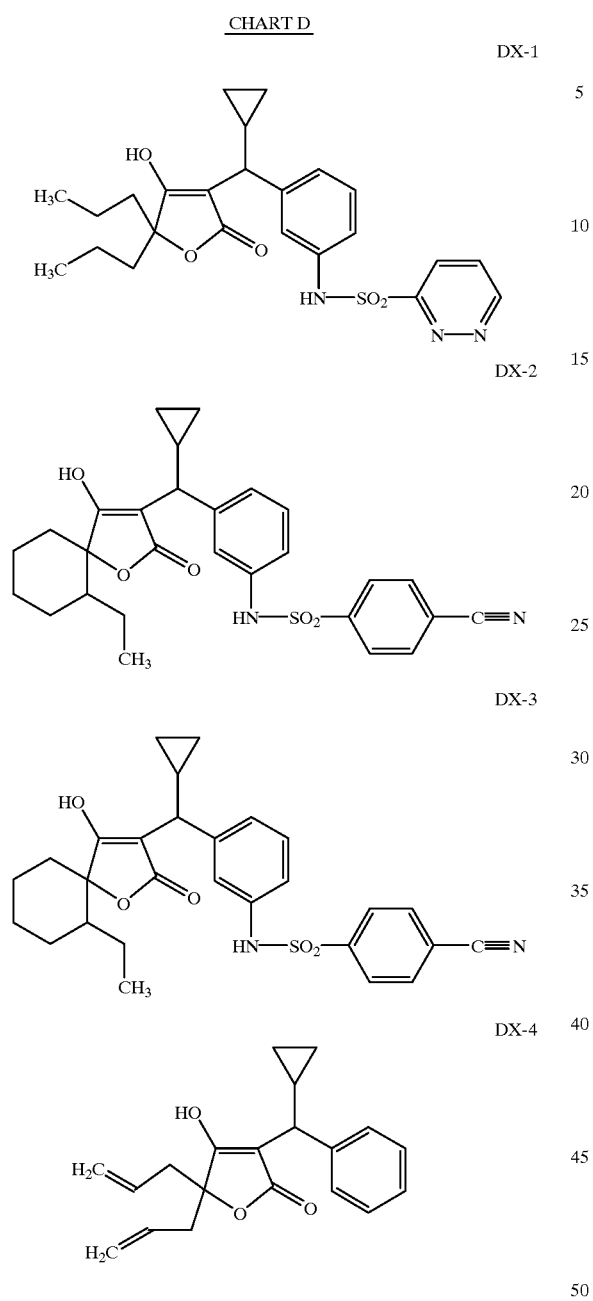
CHART A
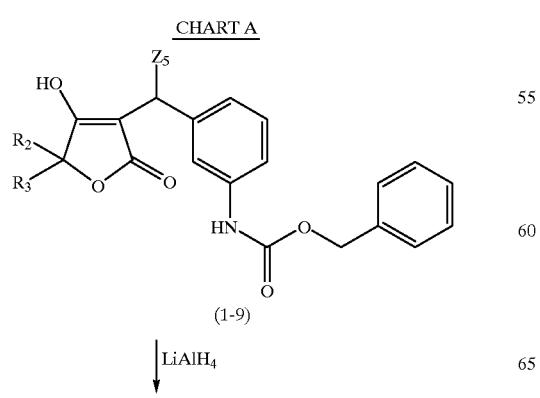
-continued
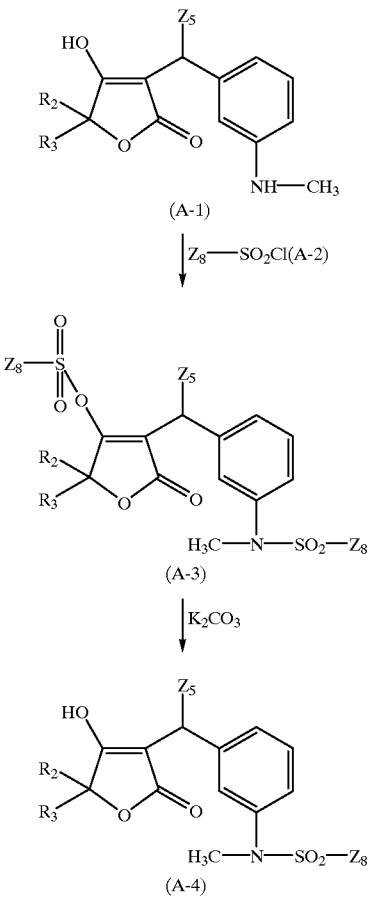

CHART B
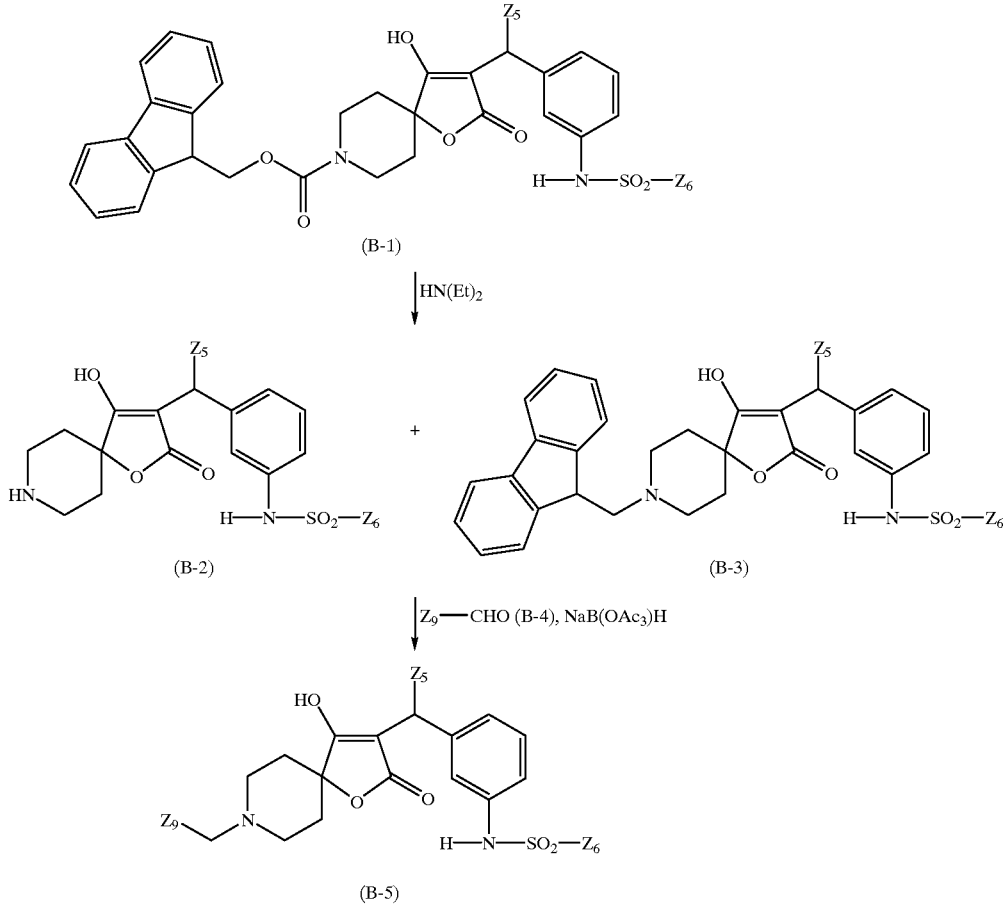

CHART C
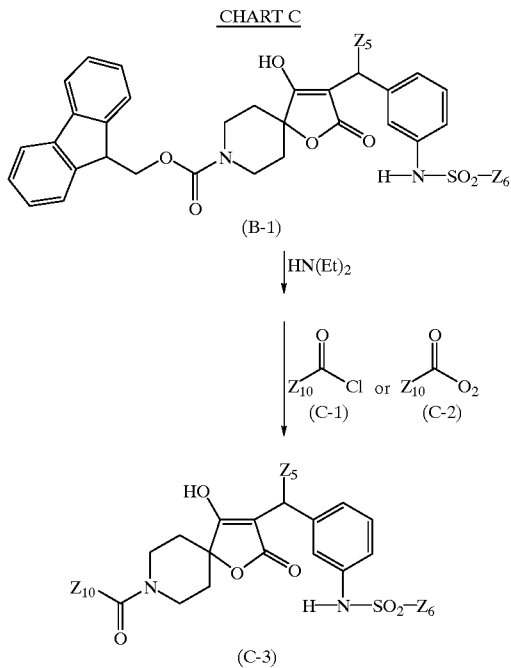
| HIV Protease Inhibitory Assay | | |
|---|---|---|
| Code Number | HIV-1 Dose | % Inhibition |
| AX-1 | 3.3 | 103.5 |
|  | 10.0 | 111.53 |
|  | 30.0 | 102.32 |
| BX-1 | 3.3 | 113.09 |
|  | 10.0 | 126.98 |
|  | 30.0 | 123.63 |
| BX-2 | 3.3 | 90.58 |
|  | 10.0 | 103.27 |
|  | 30.0 | 101.26 |
| BX-3 | 3.3 | 108.72 |
|  | 10.0 | 107 |
|  | 30.0 | 103.12 |
| BX-4 | 3.3 | 71.3 |
|  | 10.0 | 94.47 |
|  | 30.0 | 101.07 |
| BX-5 | 3.3 | 61.58 |
|  | 10.0 | 85.22 |
|  | 30.0 | 98.54 |
| CX-1 | 3.3 | 107.43 |
|  | 10.0 | 98.33 |
|  | 30.0 | 103.37 |
| CX-2 | 3.3 | 107.56 |
|  | 10.0 | 109.04 |
|  | 30.0 | 110.58 |
| DX-1 | 3.3 | 108.97 |
|  | 10.0 | 109.57 |
|  | 30.0 | 113.85 |
| DX-2 | 3.3 | 115.79 |
|  | 10.0 | 115.80 |
|  | 30.0 | 113.98 |
| DX-3 | 3.3 | 117.26 |
|  | 10.0 | 110.16 |
|  | 30.0 | 113.83 |
| DX-4 | 3.3 | 108.42 |
|  | 10.0 | 106.81 |
|  | 30.0 | 106.29 |
We claim:
1. A compound represented by the formula shown below,
BX-1
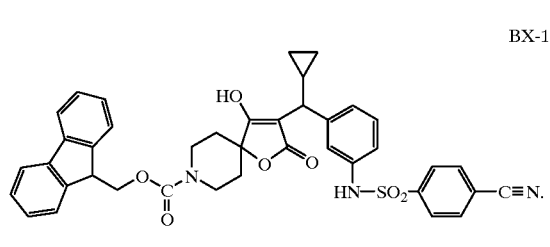
2. A compound represented by the formula shown below,
BX-2
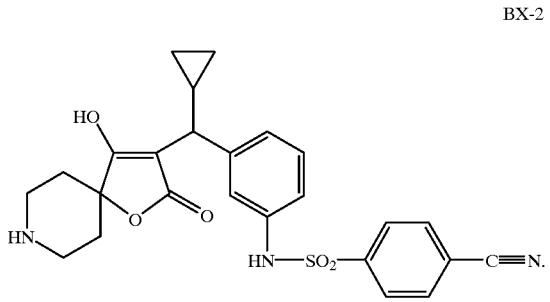
3. A compound represented by the formula shown below,
BX-3
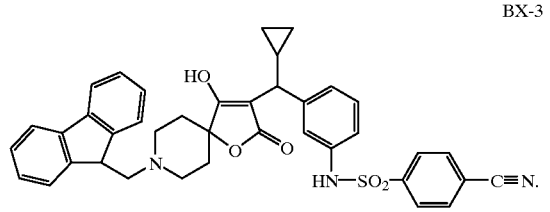
4. A compound represented by the formula shown below,
BX-4
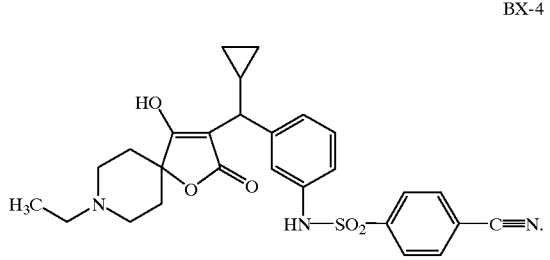

5. A compound represented by the formula shown below,
BX-5
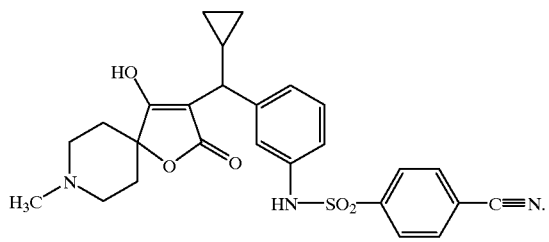
6. A compound represented by the formula shown below,
CX-1
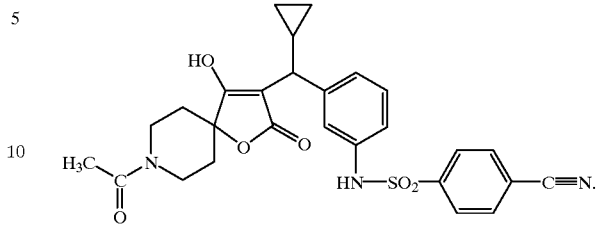
7. A compound represented by the formula shown below,
CX-2
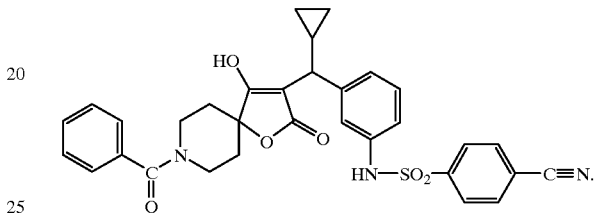
* * * * *

UNITED STATES PATENT AND TRADEMARK OFFICE
CERTIFICATE OF CORRECTION

PATENT NO. : 6,060,600
DATED : May 9, 2000
INVENTOR(S) : Chrusciel, et al.

It is certified that error appears in the above-identified patent and that said Letters Patent is hereby corrected as shown below:

On the Title Page column 1; change Chruscial et al. to Chrusciel et al.

column 1, line 5; change Robert A. Chruscial to Robert A. Chrusciel

Signed and Sealed this

Seventeenth Day of April, 2001

*Attest:*

NICHOLAS P. GODICI

*Attesting Officer*     *Acting Director of the United States Patent and Trademark Office*